United States Patent [19]

Andresen

[11] 4,051,482
[45] Sept. 27, 1977

[54] GRATICULE WITH CURSORS

[75] Inventor: Richard Paul Andresen, Arlington, Mass.

[73] Assignee: American Optical Corporation, Southbridge, Mass.

[21] Appl. No.: 680,016

[22] Filed: Apr. 26, 1976

[51] Int. Cl.$^2$ .............................................. A61B 5/04
[52] U.S. Cl. ................. 346/23; 128/2.06 G; 346/33 ME; 346/62
[58] Field of Search .................... 346/33 ME, 62, 23; 128/2.06 G, 2.05 R, 2.05 Q

[56] References Cited

U.S. PATENT DOCUMENTS

| | | | |
|---|---|---|---|
| 2,655,425 | 10/1953 | Wood | 346/23 |
| 3,893,453 | 7/1975 | Goldberg | 346/33 ME X |

Primary Examiner—Joseph W. Hartary
Attorney, Agent, or Firm—Stephen A. Schneeberger; William C. Nealon; H. R. Berkenstock, Jr.

[57] ABSTRACT

An improved graphical recorder display system for obtaining an accurate record of one or more sensed and displayed parameter values, such as associated with one or more vital signs of a patient. The system includes a writing surface medium, such as a chart paper on a drum; means for advancing the writing surface medium relative to a galvanometer pen means, the pen means being adapted for scribing on the writing surface in a direction transverse to the direction of relative advance of the chart paper; means for generating time-incremented electrical signals for extension to the galvanometer pen means during a predetermined period for scribing a graticule on the chart paper; means, such as a dither signal, selectively extendible to the galvanometer pen means for scribing one or more cursors on the chart paper; and means providing control signals representative of one or more respective vital sign parameter values for controlling the application of the dither signal to the galvanometer pen means such that the resulting cursors are in accurately timed relation to the graticule.

The dither signal is available in different amplitudes for selection by respective different parameter value signals such that the scribed cursor associated with the respective parameter values differ from one another in appearance. Further, the intensity of the scribed trace may be varied.

12 Claims, 3 Drawing Figures

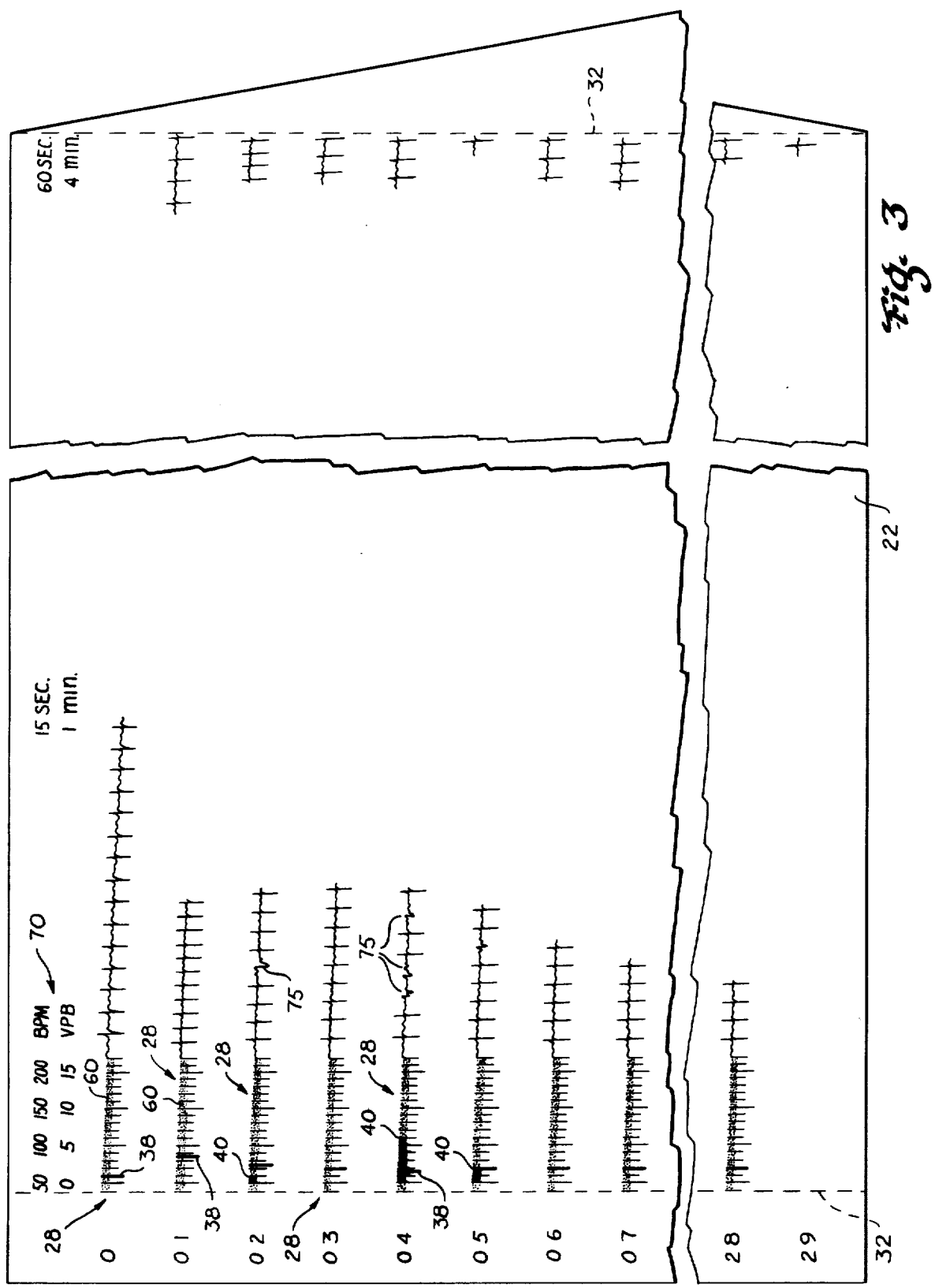

GRATICULE WITH CURSORS

BACKGROUND OF THE INVENTION

1. Field of the Invention

The present invention relates generally to the field of medical electronics. More specifically, the present invention relates to systems for recording and graphically displaying a record of the vital signs of a patient. More particularly still, the present invention relates to a graphical recorder display system for recording and displaying a summary of one or more characteristics of a patient's vital signs.

2. Description of the Prior Art

Over the years, various medical-electronic systems have been developed which aid physicians in diagnosing and providing therapy to patients. Particularly, within the area of cardiology and heart disease, there have been significant advances. In one facet of medical electronics systems, that of monitoring vital signs of a patient, various recorders and display devices have been developed for the purpose of facilitating retention and display of vital signs, data, and for the subsequent analysis thereof.

As is well known in the medical field, records such as EKG strips are taken by a physician by sensing certain physical phenomena of the patient to provide electrical signals for recording and display on a graphical recorder. Such recorders typically advance a strip or chart of paper relative to a galvanometer pen or stylus to which electrical signals indicative of vital signs have been applied. The electrical signals then serve to control the scribing of an analog record of the said vital signs on the chart paper surface. Additional electronics may provide for periodically scribing certain trend or summary information on the chart paper to summarize the occurrence of certain events during a preceding period of time.

An example of this combined capability in a vital sign display system, in which a summary of one or more characteristics of a patient's vital signs is displayed in conjunction with an analog waveform of a basic vital sign under consideration, is seen in U.S. Pat. No. 3,893,453 entitled COMPRESSED DATA DISPLAY SYSTEM issued July 8, 1975 to Goldberg et al. and assigned to American Optical Corporation. In the aforementioned patent, the chart paper is wrapped on a cylindrical drum and the galvanometer pen generally scribes a helical base line on the surface of the cylinder's chart paper in a manner which presents the recorded display data in a compact format. An EKG waveform may be the principal vital sign information traced out on the chart paper, with events such as average heart rate and/or number of premature ventricular contractions occurring during some predetermined period being indicated by a dither mark of the pen on the chart paper for reference to a graticule or scale preprinted on the charg paper.

It is possible with a system of the type described above for the chart paper to be misaligned during its installation on the drum or recorder drive and, because the electronics responsible for timing the scribing of the dither mark is keyed, at best, to the drum or recorder drive, the dither mark may be scribed at an inaccurate position on the preprinted graticule. Further, where more than one event or parameter is to be displayed on the same graticule, it becomes important that the display marks or cursors be such as to avoid ambiguity with one another, particularly if they share a common graticule when they overlap.

Accordingly, it is a principal object of the present invention to provide an improved graphical recorder display system.

It is another object of the invention to provide an improved graphical recorder system of the type which scribes one or more cursors in a graticule on the chart. Included in this object is the provision of a system of the type described in which the scribed cursors are accurately positioned relative to the graticule.

It is a still further object to provide an improved system of the type described in which a plurality of cursors sharing a common graticule avoid ambiguity.

It is an even further object of the present invention to provide an improved graphical recorder system of the type described in which the graticule and cursor arrangement facilitates analysis of the recorded data.

It is a yet further object of the invention to provide an improved recorder system of the type described for displaying and/or summarizing vital signs, as for instance ECG display and indications of related parameters such as heart rate and arrhythmia count.

SUMMARY OF THE INVENTION

According to the present invention, an improved graphical recorder display system is provided for obtaining an accurate record of one or more sensed and displayed parameter values associated with one or more vital signs of a patient. The system includes a writing surface medium, such as a chart paper on a drum; means for advancing the writing surface medium relative to a galvanometer pen means, the pen means being adapted for scribing on the writing surface in a direction transverse to the direction of relative advance of the chart paper; means for generating time-incremented electrical signals for extension to the galvanometer pen means during a predetermined period for scribing a graticule on the chart paper; means, such as a dither signal, selectively extendible to the galvanometer pen means for scribing one or more cursors on the chart paper; and means providing control signals representative of one or more respective vital sign parameter values for controlling the application of the dither signal to the galvanometer pen means such that the resulting cursors are in accurately timed relation to the graticule.

The dither signal is available in different amplitudes for selection by respective different parameter value signals such that the scribed cursor associated with the respective parameter values differ from one another in appearance. In order to further avoid ambiguity between at least two such cursors, one is provided by cumulative discrete increments of scribed dithering marks and another is a singular dithering mark of fixed and limited width. In a preferred embodiment, and ECG waveform is recorded and, at cyclical intervals, graticules are scribed and the heart rate is indicated by the former of the two cursors mentioned above, and a count of arrhythmic heart beats is indicated by the latter mentioned cursor.

To enhance the visual impact of the graticule and cursors, the graticule lines may be connected by a bar extending the length of the graticule. This connecting bar is provided by continuously applying a dither signal to the galvanometer pen means throughout the graticule scribing interval. Additionally, the galvanometer pen means includes a control capable of varying the intensity (e.g. light-dark) of the scribed trace on the chart paper such the graticule-connecting bar is normally scribed at one intensity (e.g. light) and the cursor comprised of cumulative discrete increments is represented by scribing that portion of the connecting bar at another (e.g. dark) intensity.

FIG. 3 depicts the resultant chart paper data display, including graticule and cursors generated in accordance with the present invention.

DESCRIPTION OF A PREFERRED EMBODIMENT

Figure 1:
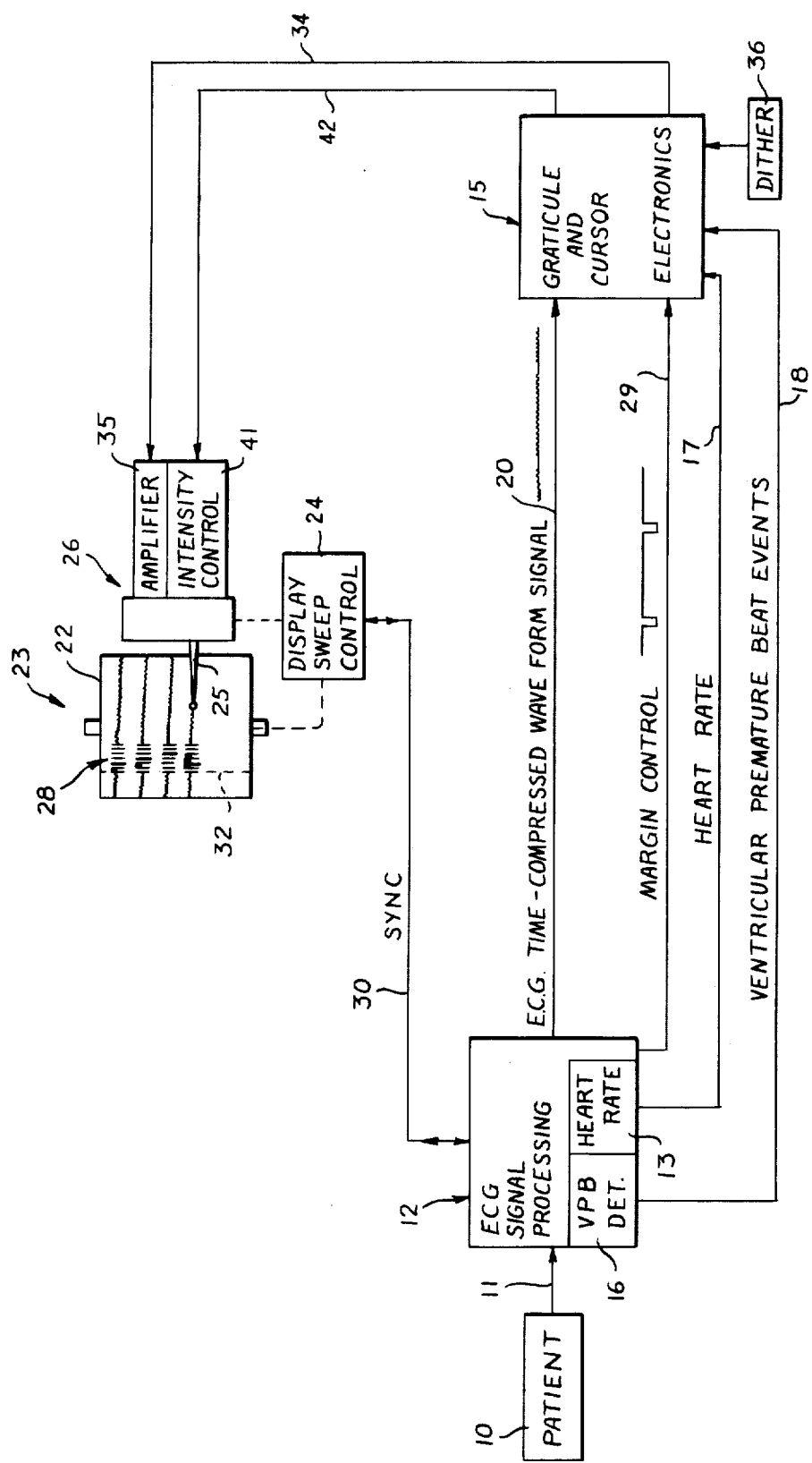
FIG. 1 is a functional block diagram of an improved graphical recorder display system incorporating novel graticule and cursor generating means.

Referring to the drawings, and particularly FIG. 1, a patient 10 is connected by ECG leads 11 to ECG signal processing electronics 12. The signal processing electronics 12 may include a time-compression system of the type disclosed in either of U.S. application Ser. No. 680,017 entitled DATA *SEQUENCE DISPLAY SYSTEM AND TIME-COMPRESSION SYSTEM THEREFOR* and filed Apr. 26, 1976 by Robert L. Cannon and Christopher C. Day and U.S. application Ser. No. 679,963 entitled TIME-COMPRESSION SYSTEM and filed Apr. 26, 1976 by Richard P. Andresen, both of which are assigned to American Optical Corporation and are incorporated by reference herein to the extent applicable to the present invention. The time-compression circuitry of ECG signal processing unit 12 serves to time-compress the incoming ECG waveform appearing on leads 11 such that the time-compresssed output includes the waveform in its entirety, with an additional time interval for the scribing of a graticule and cursors in accordance with the invention.

In addition to the time-compressing portion of signal processing unit 12, there is included a heart rate module 13 of the type discussed in the aforementioned U.S. Pat. 3,893,453 which is incorporated herein by reference. Heart rate module 13 provides a DC output voltage which is indicative of heart rate averaged over a preselected period. In the present embodiment, the selected period will correspond with the interval between successive graticule generation intervals. The average heart rate signal is extended from heart rate module 13 on conductor 17 to comparator 14 in the graticule and cursor electronics 15. The signal processing unit 12 includes a ventricular premature contraction (VPB) detector 16 for detecting ventricular premature beats of the heart (a form of ectopic beat). A premature ventricular contraction detector is disclosed in U.S. Pat. No. 3,616,790 entitled "Multiform Ventricular Premature Beat Detector" issued on Nov. 2, 1971 in the name of G. J. Harris and assigned to American Optical Corporation, the assignee of the present invention. Background information disclosed in this patent is incorporated herein by reference. The VPB Detector 16 provides an output pulse each time a ventricular premature beat is detected. The VPB output pulse is extended by conductor 18 to the clock input of an event counter 19 in the graticule and cursor electronics 15.

The ECG waveform appears at the output of signal processing unit 12 in a time-compressed format and is extended by conductor 20 to an appropriate input terminal of an analog multiplexer 21 in the electronics 15. The time-compressed waveform signal appearing on conductor 20 is displayed and recorded in its entirety on the surface of chart paper 22 which is mounted on the surface of a rotatable drum comprising part of a drum-type recorder 23. While the invention is also applicable to the scribing of a graticule and cursors on longstrip type chart recorders, it is particularly suited for application to drum-type recorders of the type described in the aforementioned U.S. Pat. No. 3,893,453. The speed of rotation of drum recorder 23 is controlled by display sweep control unit 24 which may comprise a synchronous motor mechanically engaging and rotating the drum of the recorder. The scribing stylus or pen 25 and its associated galvanometer 26 are slowly translated axially of the drum of recorder 23 such as to scribe a helical trace on the chart paper 22. The axial translation of pen 25 and galvanometer 26 is similarly controlled by display sweep control unit 24.

In a typical situation, the drum of recorder 23 might make one revolution every minute and the pen 25 is translated at a rate providing 30 lines of ECG data (0–29). Because the ECG waveform from signal processing unit 12 is in a time-compressed format, the display of the waveform will occupy less than the full circumference of chart paper 22 mounted on the recorder drum. The remaining interval in each line is available for the scribing of a graticule and attendant cursors indicative of various parameters attendant to the vital sign electrical signals of the patient 10 extended to the processing unit 12 over leads 11. The graticule 28 associated with each respective line of waveform data is located at the left side of chart paper 22 in a margin immediately to the left of the respective waveform trace line. The graticules 28 respectively associated with successive lines of waveform data are arranged in a vertical column such that the cursor scribed thereon may be quickly and easily surveyed to determine trends in the respective vital sign parameters.

The width of the margin and correspondingly, the length of each graticule 28 is selected to allow sufficient room for clear display of the graticule without inordinately compressing the ECG waveform appearing in the remainder of the line. In a representative example, the graticule 28 might extend for about 1/10 or 1/11 of each line on chart paper 22. This relationship is substantially that disclosed in the aforementioned application entitled *TIME-COMPRESSION SYSTEM* by Richard P. Andresen and will establish the necessary time-compression ratio of signal processing unit 12. This ratio of graticule margin-to-waveform display length is represented in the MARGIN CONTROL signal generated in signal-processing unit 12 and extended therefrom by conductor 29 to various circuits in the graticule and cursor electronics 15. The MARGIN CONTROL signal appears normally in the logic "1" state during the scribing of the time-compressed ECG waveform signal and goes to a logic "0" state for an interval which corresponds with the intended graticule margin width. The MARGIN CONTROL signal is repetitive and is maintained in synchronization with the drum of recorder 23 by means of a SYNC signal on conductor 30 extending from display sweep control 24 to the ECG signal processing unit 12. The bidirectional arrows on SYNC conductor 30 are intended to indicate that instead of signal processing unit 12 being slaved to display sweep control 24, the reverse may be the case if desired. As mentioned, the period of the MARGIN CONTROL signal corresponds with the period of each revolution of chart paper 22 on from recorder 23. Additionally, the MARGIN CONTROL signal appearing on conductor 29 is timed to make its transition from a logic "1" to a logic "0" state at, or just prior to, the time at which the opposite ends of the chart paper 22 mounted on the drum pass beneath the pen 25. Dotted lines 32 indicate the opposite effective ends of chart paper 22 and indicate where folds of the paper are made for insertion of these folds into a slit in the drum of recorder 23. The dotted line 32 appearing in FIG. 1 is illustrative of both effective ends of chart paper 22 and abutting relationship.

Figure 2:
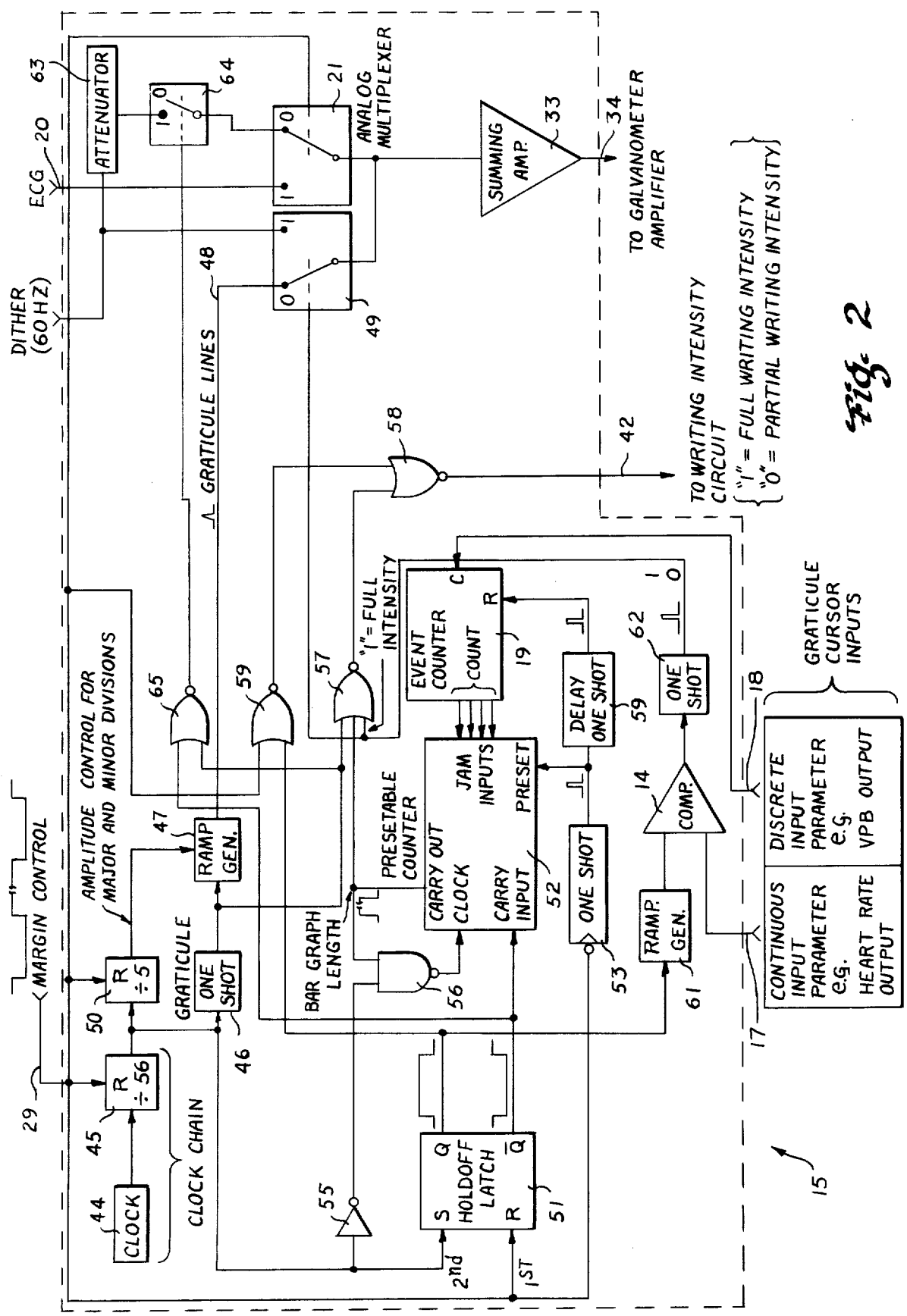
FIG. 2 is a block diagram of the novel graticule and cursor generating electronics.

Referring now to the graticule and cursor electronics 15 and particularly to the FIGS. 2 and 3, a vertical deflection electrical control signal from an output of summing amplifier 33 in the electronics unit 15 is extended over conductor 34 to the amplifier 35 associated with pen galvanometer 26 to control the deflection of pen 25 transversely of the direction in which chart paper 22 advances with the drum of recorder 23. When the time-compressed ECG waveform appearing on conductor 20 is extended through electronics 15 to conductor 34, the galvanometer 26 and pen 25 are operative to scribe the ECG waveform on chart paper 22.

During the "blanked" intervals in the time-compressed waveform signal, represented by the logic "0" state of the margin control signal, the graticule and cursor electronics 15 is operative, in conjunction with a 60 Hz dither signal from dither generator 36, to extend signals over conductor 34 to galvanometer amplifier 35 for effecting the scribing of each graticule 28 and the cursors associated therewith. The HEART RATE signal applied to electronics 15 is operative to generate a heart rate cursor 38, the VPB EVENT pulses are operative through electronics 15 to generate a VPB count cursor 40.

A second variable in the scribing action action of pen 25 is introduced by controlling the intensity or shading of the line scribed by the pen. In the illustrated embodiment, pen 25 operates through an electrical discharge to scribe on the surface of electrically sensitive chart paper 22. An intensity control unit 41 associated with pen 25 is responsive to a logic "1" control signal level extended from electronics 15 by conductor 42 to cause pen 25 to scribe with full (dark) intensity and responsive to a logic "0" signal to cause the pen to scribe at a partial intensity (gray). It will be appreciated that shading intensities other than "full" and "partial" may be employed to provide the necessary contrast. Alternatively, the scribing variable introduced by controlling the "intensity" of the scribed trace might be accomplished in other manners, such as by changing the color of ink supplied to the pen of a pen and ink-type recorder.

Referring to the graticule and cursor electronics 15 as illustrated in FIG. 2, the circuitry for generating each graticule 28 includes a clock chain comprised of a clock source 44 and divide-by-56 counter 45. A basic clock signal from clock source 44 is extended to the clock input of counter 45, the output of which is assumed to be pulses comprising graticule timing or clock pulses. The clock chain, here represented by clock source 44 and counter 45, is required to provide graticule clock pulses corresponding with each increment of the graticule to be scribed. In the present instance, it is considered desirable to have a graticule having at least 15 minor divisions, and that the graticule be preceded by a blank space which corresponds with at least one minor division of the graticule 28. In the selected example, graticule 28 includes 17 minor divisions and is preceded by a blank interval corresponding with a single minor division of the graticule. Accordingly, the margin period defined by the logic "0" state of the MARGIN CONTROL signal is divided into 18 equal increments or divisions and the clock chain ending with counter 45 is scaled to provide 18 graticule pulses during this phase of the MARGIN CONTROL signal. Clock source 44 may conveniently be provided by a counter in ECG signal processing unit 12 which is operative to load 1024 data bits into a 1024 stage random access memory during the graticule generating phase or interval of the MARGIN CONTROL signal.

The graticule timing pulses from counter 45 are extended to the input of a one-shot 46 which provides respective output pulses extended to the input of ramp generator 47. Each pulse from one-shot 46 is operative to enable ramp generator 47 for the period represented by the duration of the one-shot pulse. The period of one-shot 46 is typically quite short since the ramp generator 47 is only momentarily enabled, thereby generating a graticule line signal of short duration. The graticule line signal from the output of ramp generator 47 is extended on conductor 48 to a switch such as the "0" input of analog multiplexer 49 for selective extension through summing amplifier 33 to the galvanometer amplifier 35 for scribing the respective division lines of a graticule 28. The amplitude and duration of each graticule line signal generated by ramp generator 47 is normally such as to scribe the fine, narrow, relatively shorter minor division lines of graticule 28 which occur intermediate each major division graticule line of greater length.

The output of counter 45 in the clock chain is additionally extended to the input of divide-by-5 counter 50. The output of counter 50 is a gating signal which is extended to ramp generator 47 for controlling the amplitude of the graticule line signals generated by ramp generator 47. During the first four input pulses to divide-by-5 counter 50, the output remains low and ramp generator 47 provides the aforementioned minor division graticule signals. However, the output of counter 50 goes high at each fifth input pulse thereto and the resulting signal applied to ramp generator 47 is operative to increase the slope of the ramp such that during the time the pulse from one-shot 46 is present, the graticule line signal on conductor 48 achieves a greater amplitude for scribing a major graticule division of greater length than the four preceding or following minor divisions.

The MARGIN CONTROL signal is connected to the reset (R) inputs of divide-by-56 counter 45 and divide-by-5 counter 50 such that both counters are disabled during the waveform-tracing period of each display cycle, and are enabled during the graticule-scribing phase or margin of the cycle. Further, because counters 45 and 50 are reset to zero each time they are disabled and because clock source 44 is synchronized with the MARGIN CONTROL signal, each successive graticule 28 is in vertical registry with the one above.

Generation of a cursor representative of a vital sign discrete input parameter is controlled by the output of presetable down counter 52, which may comprise an RCA - CD 4029 UP/DOWN counter. The VPB count cursor 40 is illustrative of a cursor indicative of the value of such a discrete input parameter.

The random VPB event pulses from VPB detector 16 are extended to the clock (C) input of event counter 19. Counter 19 accumulates the count of the number of VPB events occurring during a predetermined period. The count accumulated in counter 19 is continuously extended on a plurality of parallel conductors to a respective plurality of JAM INPUTS in the presetable down counter 52. However, the count is not loaded into presetable counter 52 until a pulse appears at the PRESET input of the counter 52. The MARGIN CONTROL signal is extended to the input of one-shot 53 which responds to the negative transition of the signal to generate a preset pulse which is extended to the PRESET input of counter 52. Thus, the VPB count for each cycle of the MARGIN CONTROL signal is loaded into counter 52 at the initiation of the graticule scribing margin. The output from one-shot 53 is extended to delay one-shot 54 having its output extended to the RESET input of event counter 19 such that counter 19 is reset to zero shortly after its accumulated count has been loaded into counter 52.

The graticule clock pulses from counter 45 are extended, through inverter 55, to an input of NAND gate 56. The other input of NAND gate 56 is connected to the CARRY OUTPUT of down counter 52 so that the graticule clock pulses from inverter 55 are extended to the CLOCK input of counter 52 only when the signal voltage at CARRY OUTPUT is high, or in a logic "1" state. The CARRY OUTPUT level is normally in a high, or logic "1", state if a count other than zero remains in counter 52 or if the signal level appearing at its CARRY INPUT is a logic "1". The graticule clock pulses extended to the CLOCK input cause the down counter 52 to count down to zero, at which time the CARRY OUTPUT goes low and disables NAND gate 56 to block further clock pulses.

The graticule clock pulses from counter 45 are extended to the set (S) input of a holdoff latch flip-flop 51 and the MARGIN CONTROL signal is extended to the reset (R) input of that flip-flop. The $\overline{Q}$ output of flip-flop 51 is extended to the CARRY INPUT of down counter 52 and prevents counter 52 from counting down when its level is high (logic "1"). The $\overline{Q}$ output of flip-flop 51 will be high until the first graticule clock pulse from counter 45 sets the Q output high and the $\overline{Q}$ output low. Thus, because the $\overline{Q}$ output was then high, the counter 52 is prevented from counting the first graticule clock pulse which corresponds with the graticule line of value "zero". If, for instance, a stored count of "one" was in counter 52, the second graticule clock pulse from counter 45 (which corresponds to the graticule line value of "one") causes the count to reach "zero". The $\overline{Q}$ output of flip-flop 51 returns to the high state at the positive transition in MARGIN CONTROL signal which signifies the end of the graticule scribing margin.

The output from CARRY OUTPUT of counter 52 is also extended to an input of NOR gate 57, the output of which is extended to the input of another NOR gate 58. The output of NOR gate 58 is extended on conductor 42 to intensity control unit 41 for controlling the writing intensity of pen 25. Thus, when the CARRY OUTPUT is at a logic "1" level (as during the countdown of counter 52 to zero), the NOR gate 58 will direct a "full" (dark) writing intensity, assuming a logic "0" is applied to the other input thereto from the output of NOR gate 59.

The "full" intensity control applied to the scribing action of pen 25 is operative to "darken" an otherwise "lighter" scribed dither mark or bar 60 extending substantially continuously along graticule 28 to interconnect the division lines, as will be hereinafter explained.

The "darkened" portion of the graticule-connecting bar 60 results in the bar graph-type VPB cursur 40. Since the generation of graticule lines by ramp generator 47 and the stepping of down counter 52 are both controlled by the same train of graticule clock pulses, the bar graph comprising cursor 40 always begins and ends exactly on a graticule line without need for calibration of registration, thereby enhancing its accuracy and display value.

Referring back to the hold-off flip-flop 51, the Q output is also extended to one input of NOR gate 59. The MARGIN CONTROL signal is extended to the other input of NOR gate 59. Thus, the output of NOR gate 59 will be a logic "0" throughout all of the graticule scribing margin, with the exception of the initial blank interval between the end of the ECG waveform trace and the graticule line of value "zero", as was required for the "darker" intensity of cursor 40 previously discussed.

The output of graticule one-shot 46 is similarly extended to an input of NOR gate 57 in order that each major and minor graticule division line is scribed at "full" (dark) intensity.

Generation of a cursor representative of a vital signal continuous input parameter is controlled principally by ramp generator 61 and comparator 14. The heart rate cursor 38 is illustrative of a cursor indicative of the value of such a continuous input parameter. The output voltage from HEART RATE module 13 is extended to one input of comparator 14 for comparison with a ramp voltage extended to the other input thereof from the output of ramp generator 61. The Q output of flip-flop 51 is extended to the input of ramp generator 61 to initiate generation of the timing ramp voltage when the Q output goes high at the graticule line of value "zero". The heart rate voltage is compared with that of the timing ramp and when they are equal, the comparator 14 triggers a one-shot 62 which controls dither multiplexing and the width of the respective cursor 38. The slope of the timing ramp is selected to properly position the cursor 38 within the graticule 28 in accordance with the values ascribed to the graticule lines and generally indicated by the legend at the top of the graticule margin column. The output of one-shot 62 extends to an input of NOR gate 57 so that the dithering mark which comprises cursor 38 is scribed at "full" (dark) intensity.

Reference is made now to the generation and control of the dither signals which are extended to the galvanometer amplifier 35 for scribing the dithering marks which comprise cursor 38 and the graticule-connecting bar 60 including the bar graph cursor 40 portion thereof. The dither generator 36 of FIG. 1 is the source of a 60 Hz electrical signal at a voltage reduced from standard line voltage. This dither signal voltage is extended directly to a switch, such as the "1" input of analog multiplexer 49 and additionally, is extended through an attenuator 63 to a switch, such as the "1" input of analog multiplexer 64. The dither signal voltage of greater amplitude is available for scribing the larger amplitude dithering mark which comprises cursor 38, and the attenuated dithering signal is available for scribing the graticule-connecting bar 60 which may include cursor 40.

Normally, multiplexer 49 operates to extend the graticular line pulses from ramp generator 47 to the input of summing amplifier 33. However, when comparator 14, through one-shot 62, provides a pulse at the logic "1" level to the control input of multiplexer 49, the multiplexer is effective in a well-known manner to alternately extend the full amplitude dither signal to galvanometer amplifier 35 through summing amplifier 33 to scribe the heart rate cursor 38. The width of cursor 38 is determined by the duration of the pulse from one-shot 62 and is narrower than the spacing or interval between successive graticule divisions to avoid confusion with cursor 40 and to allow accurate determination of the indicated parameter value. It will be appreciated that this arrangement of of circuitry also permits the cursor 38 to supersede any graticule line which would have occurred at the same time.

The multiplexer 64 operates to normally block further extension of the attenuated dithering signal. However, when the output of NOR gate 65, extended to the control input of the multiplexer 64, goes to a logic "1" level, the multiplexer is effective to extend the attenuated dither signal to the "0" input of multiplexer 21. The NOR gate 65 receives inputs from the Q output of flip-flop 51 and the output of graticule one-shot 46 respectively, such that its output is a logic "1" only between graticule lines following the graticule line of value "zero". Stated another way, the attenuated dithering signal does not appear at the "o" input of multiplexer 21 either during the short "blank" interval immediately preceding the graticule line of value "zero" or during the scribing of the graticule division lines.

The ECG waveform signal (time-compressed) from processing unit 12 is connected to the "1" input of multiplexer 21. The MARGIN CONTROL signal is extended to the control input of multiplexer 21, and the multiplexer is operative, during the graticule scribing margin period when the MARGIN CONTROL signal is low, to extend any attenuated dither signal appearing at its "0" input to the galvanometer amplifier 35 through summing amplifier 33. Alternatively, when the MARGIN CONTROL signal is high the multiplexer 21 extends the time-compressed ECG waveform signal to galvanometer amplifier 35 through summing amplifier 33.

In FIG. 3, the chart paper 22 is seen to include a legent 70 which is normally preprinted and which assigns values to the respective major divisions of the graticules 28. It will be appreciated that although some small degree of misalignment may occur between the graticules 28 and legend 70, the values assigned to the major divisions of the graticule are visually and/or mentally easily translated into registry therewith. On the other hand, the problem of mislocating a cursor within a preprinted cursor is completely eliminated by synchronized timing of the graticule and cursor scribing.

Considering the first line (number "0") of displayed data, the trace will have begun with the scribing of the time-compressed ECG wave, from left to right, during which time the HEART RATE module 13 and the VPB detector 16 are monitoring the sensed vital sign signal. The graticule 28 on which the cursors representative of the values of these parameter summaries are displayed is located for convenience of visual association at the same level as the beginning of the respective wave trace. This may be accomplished by applying an upward deflection bias, not shown, to the pen 25 during the scribing of the graticules 28.

In all instances, a heart rate cursor 38 is present in graticule 28 to indicate the current average heart rate and, in those lines in which certain ectopic beats 75 are present, a bar-graph type cursor 40 indicates the number of discrete events which occurred. The cursors 38 and 40 are clearly distinguishable from one another so as to avoid ambiguity. The final, or thirtieth line (number "29") does not appear in FIG. 3 in order to illustrate that the graticules 28 have not been preprinted on paper 22.

It will be appreciated that various alternatives in the construction and implementation of the invention are apparent without departing from the general scope of the invention. Instead of presetable down counter 52, a presetable up counter may be used to invert the bar-graph cursor so that it reads from the opposite end of the graticule. Further, an additional counter which counts graticule lines can be added to reset the holdoff flip-flop 51 before the MARGIN CONTROL signal returns to the high state. This will result in a blank area following the graticule before the ECG waveform trace returns. Still further, different sources of dither could be used for the various cursors. Also, a third intensity level might be used to improve the overall appearance of the graticule and cursors. In fact, a third intensity level might take the place of different amplitudes of dither in distinguishing the different cursors from each other.

The invention may be embodied in yet other specific forms without departing from the spirit or essential characteristics thereof. Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a graphical recorded display system for obtaining a record of at least one electrical signal such as one corresponding to at least one vital sign of a patient, a scribing surface medium, scribing means, means for advancing said recording surface medium relative to said scribing means, said scribing means scribing on said scribing surface medium in scribing directions generally transverse to the direction of said advance of said scribing medium relative to said scribing means, means for sensing said at least one of said electrical signal and providing corresponding responsive electrical signals therefor, the improvement comprising:
   means for generating time-incremented electrical signals for extension to said scribing means for scribing a graticule on said scribing surface medium, said graticule being graduated in the direction of said relative advance between said scribing means and said scribing surface medium;
   means for extending said time-incremented electrical signals to said scribing means during a predetermined period for scribing said graticule;
   means providing at least one electrical control signal respectively representative of the value of a respective parameter of a said electrical signal measured during a predetermined period of time, said at least one parameter value control signal having a particular time relationship with said graticule signals determined by said value of said parameter;
   means selectively extendible to said scribing means for scribing a cursor on said scribing surface medium; and
   means responsive to said at least one parameter value signal for extending said cursor scribing means to said scribing means during said graticule scribing period to scribe a respective cursor on said scribing surface medium in timed relation to said graticule, thereby to indicate the value of said at least one respective parameter.

2. The system of claim 1 wherein said means selectively extendible to said scribing means for scribing a cursor comprises electrical dither signal means.

3. The system of claim 2 wherein said parameter value signal providing means provides a plurality of electrical signals, a respective signal of said plurality for each of a respective plurality of parameters of at least one said electrical signal, and said plural parameter value signals being respectively operative to control the scribing of a respective plurality of cursors upon said scribing surface medium.

4. The system of claim 3 wherein said electrical dither signal means comprises first and second different dither signals, said plural parameter value signals comprise first and second different parameter value signals, and said dither signal-extending means is responsive to respective said first and second parameter value signals for extending respective said first and second dither signals to said scribing means thereby to scribe respective different cursors.

5. The system of claim 4 wherein said first and second parameter value signals respectively comprise a signal representative of a continuous input parameter and a signal representative of a discreet input parameter, said first parameter value signal is operative through its control of a respective said dither signal to scribe a cursor of fixed, limited size measured in the direction of said graticule graduations, and said second parameter value signal is operative through its control of a respective said dither signal to scribe a cursor comprised of cumulative discreet increments.

6. The system of claim 5 wherein said means for extending said graticule scribing signals to said scribing means is disabled when said first parameter value signal operates to extend its respective said dither signal to scribe said cursor of fixed limited size.

7. The system of claim 2 wherein said electrical dither signal means is extended to said scribing means throughout said predetermined period during which said graticule is scribed to additionally scribe a substantially continuous bar interconnecting the graduation lines of said graticule, said scribing means is responsive to an intensity control signal for varying the writing intensity of the scribing means, and including means responsive to said at least one parameter value signal for applying an intensity control signal to said scribing means for scribing a said at least one cursor and the lines of said graticule in an intensity different than the intensity of said graticule connecting bar.

8. The system of claim 7 wherein a said parameter value signal is operative to apply a said intensity control signal to said scribing means for scribing a substantially continuous first portion of said graticule connecting bar in an intensity different than the remaining portion thereof, a said at least one cursor being represented by the intensity of said graticule connecting bar first portion.

9. The system of claim 8 wherein said electrical dither signal means is operative to provide dither signals of two different amplitudes, said parameter value signal means provide two electrical signals each respectively representative of a different parameter of a said at least one electrical signal, and said means for extending a cursor scribing means to said scribing means is responsive to one of said two parameter value signals for extending a dither signal of one amplitude and alternately responsive to the other of said parameter value signals for extending a dither signal of the other amplitude, thereby to scribe respectively different cursors.

10. The system of claim 9 wherein said dither signal of greater amplitude is extended to said scribing means for an interval shorter than the interval between successive said graticule scribing signals to scribe the respective cursor for one said parameter value signal and said dither signal of lesser amplitude is extended to said scribing means for an interval substantially as great as the interval between at least successive said graticule scribing signals to scribe the respective cursor for the other of said parameter value signals.

11. The system of claim 2 wherein said scribing means is responsive to an intensity control signal for varying the writing intensity of said means, and including means responsive to said at least one parameter value signal for applying an intensity control signal to said scribing means to control the intensity of scribing of said at least one respective cursor.

12. The system of claim 3 wherein said scribing means is responsive to an intensity control signal for varying the writing intensity of said means, and including means responsive to at least one of said plurality of parameter value signals for applying an intensity control signal to said scribing means to vary the intensity of scribing of at least one respective cursor from that of at least one other cursor of said plurality.

* * * * *